United States Patent [19]

Shockey et al.

[11] Patent Number: 5,120,323
[45] Date of Patent: Jun. 9, 1992

[54] TELESCOPING GUIDE CATHETER SYSTEM

[75] Inventors: Rick L. Shockey, Eagan, Minn.;
Donald S. Baim, Newton, Mass.;
Kevin L. Cronk, Maple Grove; Rocky
R. J. Campbell, Maple Plain, both of
Minn.

[73] Assignee: Schneider (USA) Inc., Minneapolis, Minn.

[21] Appl. No.: 730,373

[22] Filed: Jul. 11, 1991

Related U.S. Application Data

[63] Continuation of Ser. No. 464,324, Jan. 12, 1990, abandoned.

[51] Int. Cl.⁵ ............................................. A61M 25/00
[52] U.S. Cl. ................................. 604/282; 606/194; 128/657
[58] Field of Search ........................... 606/192, 194; 604/96–103, 265, 280, 282; 128/656–658, 772

[56] References Cited

U.S. PATENT DOCUMENTS

| | | |
|---|---|---|
| 3,485,234 | 12/1969 | Stevens . |
| 4,323,071 | 4/1982 | Simpson et al. . |
| 4,564,014 | 1/1986 | Fogarty et al. ............ 606/194 |
| 4,581,017 | 4/1986 | Sahota . |
| 4,616,652 | 10/1986 | Simpson ............... 128/657 X |
| 4,636,346 | 1/1987 | Gold et al. . |
| 4,669,465 | 6/1987 | Moore . |
| 4,774,949 | 10/1988 | Fogarty . |
| 4,784,636 | 11/1988 | Rydell . |
| 4,817,613 | 4/1989 | Jaraczewski et al. ........... 128/658 |
| 4,863,442 | 9/1989 | DeMello et al. ............. 604/282 |
| 4,883,459 | 11/1989 | Calderon ................. 604/28 |
| 4,886,506 | 12/1989 | Lougren et al. ............ 604/280 |
| 4,898,591 | 2/1990 | Jang et al. ............... 604/282 |
| 4,932,413 | 6/1999 | Shockey et al. ........... 128/657 |
| 4,976,689 | 12/1990 | Buchbinder et al. .......... 604/95 |
| 4,976,691 | 12/1990 | Sahota ................... 604/96 |

FOREIGN PATENT DOCUMENTS

| | | |
|---|---|---|
| 277366 | 8/1988 | European Pat. Off. . |
| 303487 | 2/1989 | European Pat. Off. . |

Primary Examiner—John D. Yasko
Assistant Examiner—Adam J. Cermak
Attorney, Agent, or Firm—Haugen and Nikolai

[57] ABSTRACT

The guide catheter system for use in the treatment of coronary artery disease includes a first single-lumen catheter of a relatively large internal diameter to pass a second guide catheter therethrough. The first guide catheter comprises an elongated flexible tube having a stainless steel braid embedded in the wall thereof for imparting desired torqueability characteristics to it. The first guide catheter is intended to be inserted at an appropriate point in the vascular system and then advanced until its distal end reaches the coronary ostium. The second guide catheter is fabricated by extruding a plastic, such as polyurethane thermoplastic resin over a tubular Teflon ® core and because it is to be used within the lumen of the first catheter, it need not include a braided structure within its walls to prevent it from kinking. This allows the second catheter to be sufficiently slim to permit it to be advanced into a coronary artery while allowing fluids to be perfused between the outer wall of the second guide and the inner wall of the first guide catheter while still providing a sufficiently large inner lumen to pass a working catheter, e.g., an angioplasty or atherectomy catheter. An atraumatic tip is attached to the distal end of the second guide catheter.

19 Claims, 1 Drawing Sheet

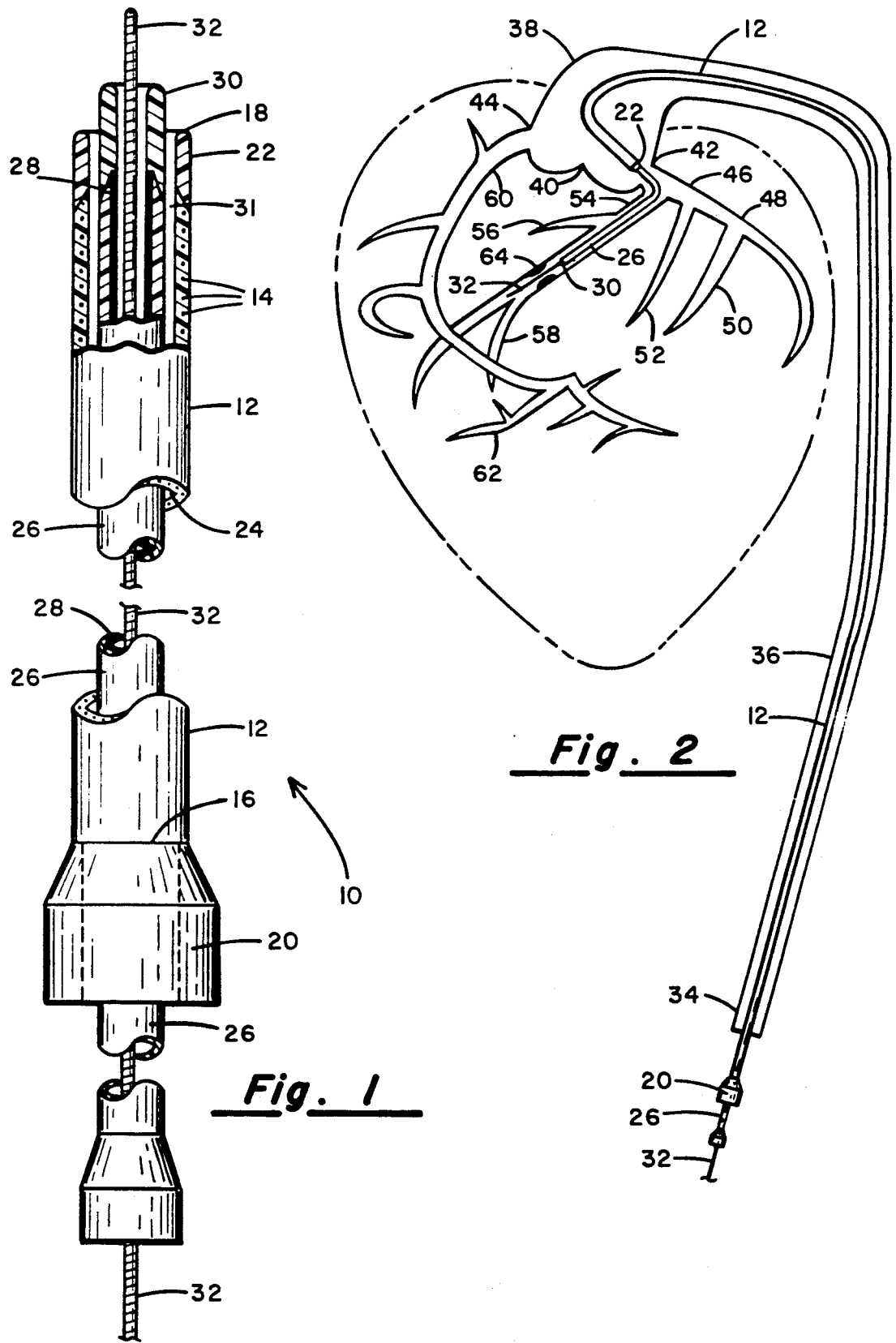

TELESCOPING GUIDE CATHETER SYSTEM

This is a continuation of copending U.S. application Ser. No. 07/464,324, filed on Jan. 12, 1990 now abandoned.

BACKGROUND OF THE INVENTION

I. Field of the Invention

This invention relates generally to improved catheter apparatus for facilitating the recanalization of a stenosed coronary artery and more particularly to an improved guide catheter system whereby a guide catheter member can be advanced beyond the coronary ostium and into the coronary artery itself up to the point of the stenosis.

II. Discussion of the Prior Art

In treating coronary artery disease, a variety of surgical techniques are employed to recanalize an occluded or partially occluded artery segment without requiring open heart surgery. Using the technique pioneered by A. Gruntzig, a catheter having an expander (balloon) at its distal end is routed through the vascular system and ultimately into the coronary artery with the balloon being juxtaposed with the stenotic lesion. Once so positioned, the balloon is inflated to compress the plaque into the wall of the blood vessel, thus restoring patency.

In another procedure, referred to as an atherectomy, a catheter having a rotatable cutter at its distal tip is advanced through the vascular system and when the tip is made to abut the atheroma, a motor at the proximal end of the catheter is used to drive the cutter to surgically "tunnel" through the lesion. In this regard, reference is made to the Rydell U.S. Pat. No. 4,784,636, assigned to applicant's assignee.

Still others have incorporated a fiber optic bundle in a catheter and a laser is used to burn through the plaque comprising the arterial blockage. In this regard, reference is made to the Moore et al U. S. Pat. No. 4,669,465, assigned to GV Medical, Inc., of Minneapolis, Minn.

The foregoing are exemplary of working catheters, i.e., the catheters that are directly involved in the recanalization through expansion, excision or ablation. To properly position the working catheter, it is also necessary that a guide catheter be utilized. A guide catheter of the prior art typically comprises an elongated, flexible tube having an internal lumen sufficiently large to receive and pass the working catheter therethrough. In that the catheters are generally introduced into the femoral artery and then advanced through the vascular system to the heart, the guide catheter must possess a characteristic of "torqueability" meaning that it can transmit a twisting force applied at its proximal end to the distal end to facilitate the ability to steer it through the appropriate vascular branches. The torqueability characteristic is achieved by the appropriate choice of materials for the guide catheter shaft or by incorporating a braided sheath of wire strands embedded in the wall of the guide catheter. Those wishing further information concerning the construction of a typical prior art guide catheter are referred to the Stevens U.S. Pat. No. 3,485,234, assigned to the Cordis Corporation of Miami, Fla.

When it is considered that the lumen of the guide catheter must be large enough to pass the working catheter and that the guide catheter shaft must exhibit acceptable torqueability and stiffness characteristics, it tends to dictate a guide catheter having a relatively large outside diameter. In fact, it has not been possible in the past to advance the distal end of the conventional guide catheter beyond the coronary ostium. Where the site of the lesion in the coronary artery is several centimeters beyond the ostium and it becomes necessary during the recanalization procedure to exchange working catheters, damage may be done to the delicate tissue of the intima.

SUMMARY OF THE INVENTION

In accordance with the present invention, a system of guide catheters is provided whereby a guide catheter can be configured sufficiently small in outside diameter that it will pass distally of the ostium into the coronary artery to be treated while maintaining a sufficiently large internal diameter for allowing a working catheter to be passed therethrough and guided thereby. More specifically, the guide catheter system includes a somewhat conventional guide catheter of the type described above, but instead of passing the working catheter directly through its lumen, a second guide catheter is telescopingly received within the lumen of the first guide catheter. The second guide catheter comprises an elongated thin-wall tube of polytetrafluoroethylene (Teflon ®) which is coated on its exterior with a blend of polyurethanes. Because the second guide catheter is to be passed through the lumen of the first guide catheter, it does not require a braided layer to provide the torqueability necessary to route the guide catheter from its femoral artery entry point to the heart. Instead, it tracks the lumen of the first guide catheter. Because the need for a braided layer is obviated, it can be made of a sufficiently thin wall that its outside diameter is sufficiently small that the second guide catheter can be advanced beyond the ostium and into the coronary artery itself. To minimize damage to the endothelial layer, the second guide catheter is equipped with a soft tip which is appropriately rounded to avoid sharp edges which can damage the arterial wall. The soft tip may preferably be formed from a polyurethane resin exhibiting low durometer as compared to the durometer of the polyurethane blend coating the Teflon tubular core. By lining the second guide catheter with the Teflon core, its trackability and pushability property is enhanced. The Teflon layer provides a low coefficient of friction with the working catheter to be inserted.

With the second guide catheter advanced so that its distal end portion is contained within the coronary artery to be treated, it provides backup support for the blood vessel during the recanalization procedure and allows repeated exchanges of working catheters with a minimum of damage to the intima.

The foregoing features, objects and advantages of the invention will become more apparent to those skilled in the art from the following detailed description of a preferred embodiment, especially when considered in conjunction with the accompanying drawings in which like numerals in the several views refer to corresponding parts.

DESCRIPTION OF THE DRAWINGS

FIG. 1 is a side view, partially cross-sectioned of the guide catheter system of the present invention; and FIG. 2 is a diagram illustrating the use of the present invention in recanalizing a stenosed coronary arterial blood vessel.

DESCRIPTION OF THE PREFERRED EMBODIMENT

Referring first to FIG. 1, there is indicated generally by numeral 10 the guide catheter system in accordance with the present invention. It is seen to include a first, relatively large diameter guide catheter 12, comprising an elongated, flexible plastic tube which would typically be approximately 100 cms. in length and fabricated primarily from a blend of polyurethanes and containing a braided wire sheath 14 within its walls. In that the outer guide catheter 12 is intended to be routed through the vascular system from a peripheral site such as an incision into the femoral artery, the wire braid affords the desirable torque properties whereby twisting the proximal end 16 will transmit a corresponding torque to the distal end 18 of the catheter 12. The catheter 12 may be in the range of from about 9 French to 5 French and designed to have an internal lumen in the range of from 7 French to 3.5 French. Bonded to the proximal end 16 of the outer catheter 12 is a conventional catheter hub 20. The catheter structure thus far described may be produced in accordance with the Stevens U.S. Pat. No. 3,485,234 which describes a manufacturing process whereby a catheter is produced having a precisely dimensioned lumen and a braided wire sheath disposed entirely within the plastic comprising the catheter's wall.

To reduce the likelihood and/or extent of trauma to the endothelial lining of the blood vessels through which the outer catheter 12 is routed, it is preferably provided with an atraumatic tip 22 which is appropriately attached to the end of the outer tubing member. The soft tip 22 will typically be formed from a polyurethane blend exhibiting a lower durometer than the plastic comprising the remainder of the catheter. It may be attached and otherwise configured as set out in the Van Tassel et al. U.S. Pat. No. 4,531,943 assigned to applicant's assignee.

Coaxially disposed and loosely fitting within the lumen 24 of the first or outer catheter 12 is a second catheter 26 which is of a somewhat greater length than the first catheter 12. The body of the catheter 26 comprises an internal tubular core 28 which is made from polytetrafluoroethylene (Teflon®) having a wall thickness of approximately 0.0005 inches The Teflon tube, while supported on a cylindrical mandrel, is then coated with a suitable plastic, preferably a blend of polyurethanes so that the composite outside diameter is in the range of from 8 French to 3 French.

As mentioned above, the inside diameter of the outer guide catheter 12, if designed to be 7 French, leaves a predetermined clearance between the two when a second catheter 26 of, say, 6 French, is telescopingly received within the lumen 24 of the outer catheter 12. This permits the perfusion or aspiration of liquids through the annular gap between inner wall of the outer catheter 12 and the outer wall of the inner catheter 26.

Appropriately bonded to the distal end portion of the second or inner catheter 26 is an atraumatic tip 30 again formed from a suitable plastic material exhibiting a low durometer rating.

The catheter 26, being 6 French, may have an internal diameter of 0.063 inches which is sufficiently large to pass a working catheter (not shown) therethrough. As mentioned above, the working catheters employed may include those for angiography, atherectomy, as well as various pressure monitoring or fiber optic devices.

Shown threaded through the lumen of the inner tubular catheter 26 is an elongated flexible, helically wound stainless steel guidewire 32.

Having described the constructional features of the guide catheter system of the present invention, consideration will next be given to its mode of use. In this regard, reference is made to FIG. 2 which diagrammatically depicts the various coronary arterial blood vessels, both anterior and posterior with the remainder of the heart eliminated. Thus, numeral 34 identifies the femoral artery leading to the descending aorta 36, the aortic arch 38 and the aortic valve 40. Located adjacent the aortic arch 38 and slightly above the valve 40 is the left coronary ostium 42 and the right coronary ostium 44.

Leading away from the ostium 42 is the left coronary artery 46 which joins to the circumflex branch 48 from which the obtuse marginal branch 50 and the intermediate branch 52 extend.

The left anterior descending artery is identified by numeral 54 and branching from it are the septal arteries 56 and 58.

Extending from the right coronary ostium 44 is the right coronary artery 60 which leads to the posterior descending artery 62. Let it be assumed that a stenosis exists at 64 in the left anterior descending artery 54 and that it is desired to treat the lesion with an angioplasty balloon-type working catheter. In carrying out the procedure, an incision is made and an introducer (not shown) is inserted into the femoral artery 34. The first catheter 12 is then passed retrograde up the descending aorta 36 and beyond the aortic arch 38 until its distal tip 22 abuts the coronary ostium 42. Next, a guidewire 32 is passed through the lumen of the first guide catheter 12 and maneuvered by twisting and advancing distally until the guidewire passes down the left anterior descending artery 54 and beyond the location of the lesion 64. Once the guidewire 32 is so positioned, the telescoping guide catheter 26 is passed over the wire 32 by feeding the distal tip 30 over the guidewire and feeding it through the hub 20 of the outer guide catheter 12 and thence through the lumen 24 thereof until it exits the distal end 18 of the outer catheter through the left coronary ostium 42 and down the left anterior descending branch 54. Once the distal tip 30 of the inner telescoping guide catheter 26 is proximate the site of the lesion, the working catheter (not shown) with its distal balloon may now be fed through the lumen 31 of the inner guide catheter and over the guide wire 32. Because the interior wall of the inner guide catheter is lined with a layer of a lubricious plastic, such as Teflon, the coefficient of friction between the working catheter and the wall of the inner guide catheter is low, thus enhancing the trackability of the working catheter through the lumen of the inner guide catheter 26. Once the distal balloon of the working catheter is advanced across the stenosis, dilatation of the affected blood vessel can take place. Once the balloon has been advanced across the lesion, it is the physician's choice whether to pull the inner guide back into the lumen of the outer guide or not.

It may also occur that the physician will want to withdraw one working catheter in favor of a replacement working catheter. By leaving the internal guide catheter 26 in position, the exchange may take place without repeatedly drawing the working catheter back and forth over the endothelial lining of the blood vessel.

Instead, the arterial branch remains supported by the guide catheter 26 during the exchanges.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method of performing recanalization of a stenosed coronary artery of interest comprising the steps of:

introducing a first elongated, hollow, flexible, plastic, relatively large diameter, reinforced-wall torque-transmitting guide catheter having a proximal end and a distal end at a predetermined location in the vascular system and advancing the first guide catheter until the distal end thereof reaches the coronary ostia;

inserting a second, elongated, hollow, flexible, plastic, relatively smaller diameter unreinforced guide catheter having a tubular core a polytetrafluoroethylene polymeric material sheathed in an outer cylindrical coating of a second polymeric material and a distal tip member of a material of relatively low durometer relative to the other materials of the second guide catheter affixed to the distal end of the second guide catheter, wherein the tip member is further characterized by a distal end shaped to encounter and minimize damage to the endothelial lining of coronary artery of interest by the advancing second guide catheter;

advancing the second guide catheter until the distal end of the second catheter passes beyond the distal end of the first guide catheter and into the coronary artery of interest adjacent the stenosis to be canalized;

slidably introducing a working catheter having a proximal end and a distal end into the hollow tubular core of the second guide catheter and advancing the working catheter therealong until the distal end of the working catheter passes through and extends beyond the distal end of the second guide catheter and into the stenosed area of the coronary artery of interest; and using the working catheter to accomplish recanalization.

2. The method of claim 1 wherein the outside diameter of the second guide catheter is in the range of from about 6.5 French to 3 French and the inside diameter of the first guide catheter is in the range of from about 7 French to 3.5 French.

3. A telescoped dual guide catheter system for use in performing artery transluminal angioplasty or atherectomy procedures in a coronary artery of interest having the ability to navigate coronary arteries comprising:

an outer guide catheter comprising an elongated, flexible plastic tuber having a proximal end and a distal end, having an outside diameter small enough to pass through the arterial vascular system from an introducer site to the coronary ostia, the outer guide catheter further describing an internal lumen of a relatively large size extending from the proximal end to the distal end and having a tube wall characterized by reinforcing means internal to the tube wall for providing the necessary torque transmission required to enable routing of the outer guide catheter through the arterial vascular system; and an inner elongated guide catheter adapted to be telescopingly received within and passed through the lumen of the outer guide catheter and including flexible tubular core of a lubricous material constructed without reinforcing means surrounded by an outer coating of a polymeric material and having a proximal end, a distal end and an outside diameter sufficiently small to fit with a predetermined clearance within the lumen of the outer guide catheter;

wherein the distal end of the unreinforced inner guide catheter is adapted to pass beyond the distal end of the outer guide catheter and navigate vascular areas beyond the distal end of the outer guide catheter through which the outer guide catheter itself cannot be safely passed including the area beyond the coronary ostia into a coronary artery of interest to be recanalized; and wherein the lumen of the tubular core of the inner guide catheter is of sufficient diameter to pass a working catheter therethrough.

4. The telescoped dual guide catheter system of claim 3 further including a tubular tip member of a polymer material of relatively low durometer affixed to the distal end of the inner guide catheter, wherein the tip member is further characterized by a rounded distal end to encounter and minimize damage to the endothelial lining of the vascular system including the coronary artery of interest.

5. The telescoped dual guide catheter system of claim 4 wherein the reinforcing means internal to the tube wall of the outer guide catheter is braided wire;

wherein the core of the inner guide catheter is polytetrafluoroethylene; and wherein the outer coating comprises a blend of polyurethane.

6. The telescoped dual guide catheter system of claim 5 wherein the polymer tip material is a relatively soft polyurethane.

7. The telescoped dual guide catheter as in claim 6 further including a molded plastic hub affixed to the proximal end of the inner guide catheter.

8. The telescoped dual guide catheter of claim 6 wherein the wall of the inner catheter is thinner than the wall of the outer catheter tube.

9. The telescoped dual guide catheter as in claim 5 further including a molded plastic hub affixed to the proximal end of the inner guide catheter.

10. The telescoped dual guide catheter of claim 5 wherein the wall of the inner catheter is thinner than the wall of the outer catheter tube.

11. The telescoped dual guide catheter system of claim 4 wherein the polymer tip material is a relatively soft polyurethane.

12. The telescoped dual guide catheter as in claim 4 further including a molded plastic hub affixed to the proximal end of the inner guide catheter.

13. The telescoped dual guide catheter system of claim 3 wherein the outside diameter of the smaller inner guide catheter is in the range of from about 6.5 French to 3 French and the corresponding inside diameter of the large outer guide catheter is in the range of from about 7 to 3.5 French.

14. The telescoped dual guide catheter as in claim 13 further including a molded plastic hub affixed to the proximal end of the inner guide catheter.

15. The telescoped dual guide catheter of claim 13 wherein the wall of the inner catheter is thinner than the wall of the outer catheter tube.

16. The telescoped dual guide catheter system of claim 3
   wherein the reinforcing means internal to the tube wall of the outer guide catheter is braided wire;
   wherein the core of the inner guide catheter is polytetrafluoroethylene; and
   wherein the outer coating comprises a blend of polyurethane.

17. The telescoped dual guide catheter as in claim 3 further including a molded plastic hub affixed to the proximal end of the inner guide catheter.

18. The telescoped dual guide catheter of claim 3 wherein the wall of the inner catheter is thinner than the wall of the outer catheter tube.

19. A telescoped dual guide catheter system for use in performing artery transluminal angioplasty or atherectomy procedures in a coronary artery of interest having the ability to navigate coronary arteries comprising:
   an outer guide catheter comprising an elongated, flexible plastic tube having a proximal end and a distal end, having an outside diameter small enough to pass through the arterial vascular system from an introducer site to the coronary ostia, the outer guide catheter further describing an internal lumen of a relatively large size extending from the proximal end to the distal end and having a tube wall characterized by a braided metal reinforcing layer internal to the tube wall for providing the necessary torque transmission required to enable routing of the first guide catheter through the arterial vascular system; and
   an inner elongated guide catheter adapted to be telescopingly accommodated by, received within, and passed through the lumen of the outer guide catheter and including an unreinforced flexible tubular core of a lubricous polytetrafluoroethylene surrounded by an outer coating of a polyurethane blend material and having a proximal end, a distal end and an outside diameter sufficiently small to fit with a predetermined clearance within the lumen of the outer guide catheter;
   wherein the distal end of the unreinforced inner guide catheter is adapted to pass beyond the distal end of the outer guide catheter and navigate vast vascular areas beyond the distal end of the outer guide catheter through which the outer guide catheter itself cannot be safely passed including the area beyond the coronary ostia into a coronary artery of interest to be recanalized;
   wherein the lumen of the tubular core of the inner guide catheter is of sufficient diameter to pass a working catheter therethrough;
   a tubular tip member of a polymer material of relatively low durometer polyurethane affixed to the distal end of the inner guide catheter, the tip member being further characterized by a rounded distal end to encounter and minimize damage to the endothelial lining of the coronary artery of interest.

* * * * *

UNITED STATES PATENT AND TRADEMARK OFFICE
CERTIFICATE OF CORRECTION

PATENT NO. : 5,120,323
DATED : June 9, 1992
INVENTOR(S) : Rick L. Shockey et al It is certified that error appears in the above-identified patent and that said Letters Patent is hereby corrected as shown below:

Column 5, line 27, delete "a", and insert --of--

In column 5, line 63, delete "tuber", and insert -- tube -- .

In column 6, line 6, delete "and".

In column 6, line 10, delete "lubricous" and insert -- lubricious -- .

In column 6, line 37, after "4", insert -- : -- .

In column 7, line 2, after "7", insert -- French -- .

In column 7, line 10, after "3", insert -- : -- .

In column 8, line 10, delete "lubricous" and insert -- lubricious -- .

Signed and Sealed this

Fourteenth Day of September, 1993

*Attest:*

*Attesting Officer*

BRUCE LEHMAN

*Commissioner of Patents and Trademarks*